(12) United States Patent
Silveira et al.

(10) Patent No.: US 11,988,652 B2
(45) Date of Patent: May 21, 2024

(54) PACKED TIP ELECTROSPRAY EMITTER (71) Applicant: Thermo Finnigan LLC, San Jose, CA (US)

(72) Inventors: Joshua A. Silveira, San Jose, CA (US); Dale Lindseth, San Jose, CA (US); Gary A. Schultz, Ithaca, NY (US); Eloy R. Wouters, San Jose, CA (US); Michael L. Poltash, Fremont, CA (US); Brandon Howard Robson, San Jose, CA (US)

(73) Assignee: Thermo Finnigan LLC, San Jose, CA (US)

( * ) Notice: Subject to any disclaimer, the term of this patent is extended or adjusted under 35 U.S.C. 154(b) by 479 days.

(21) Appl. No.: 16/951,909

(22) Filed: Nov. 18, 2020

(65) Prior Publication Data

US 2022/0155267 A1 May 19, 2022

(51) Int. Cl.
*G01N 30/72* (2006.01)
*G01N 30/14* (2006.01)
*G01N 30/60* (2006.01)
*G01N 33/68* (2006.01)
*H01J 49/00* (2006.01)
*H01J 49/04* (2006.01)
*H01J 49/16* (2006.01)
*G01N 30/02* (2006.01)
*G01N 30/04* (2006.01)

(52) U.S. Cl.
CPC ......... *G01N 30/7233* (2013.01); *G01N 30/14* (2013.01); *G01N 30/60* (2013.01); *G01N 33/6848* (2013.01); *H01J 49/0031* (2013.01); *H01J 49/004* (2013.01); *H01J 49/0436* (2013.01); *H01J 49/165* (2013.01); *G01N 2030/027* (2013.01)

(58) Field of Classification Search
CPC .... G01N 30/7233; G01N 30/14; G01N 30/60; G01N 30/7266; G01N 33/6848; G01N 2030/027; H01H 49/0031; H01H 49/004; H01H 49/165; H01H 49/167; H01H 49/0436
USPC ....................................................... 250/288
See application file for complete search history.

(56) References Cited

U.S. PATENT DOCUMENTS

| | | | |
|---|---|---|---|
| 5,572,023 | A | 11/1996 | Caprioli |
| 5,993,633 | A | 11/1999 | Smith et al. |
| 6,315,905 | B1 | 11/2001 | Settlage et al. |
| 7,544,932 | B2 | 6/2009 | Janini et al. |

(Continued)

FOREIGN PATENT DOCUMENTS

WO    2009123415 A1    10/2009

OTHER PUBLICATIONS

Tong et al., "Identification of Proteins in Complexes by Solid-Phase Microextraction/Multistep Elution/Capillary Electrophoresis/Tandem Mass Spectrometry," Analytical Chemistry, vol. 71, No. 13, Jul. 1, 1999, pp. 2270-2279.

(Continued)

*Primary Examiner* — Kiet T Nguyen (57) ABSTRACT

Packed-tip electrospray ionization (ESI) emitters for mass spectrometry are described. In one aspect an ESI emitter stores a first type of particle. A liquid chromatography (LC) column is coupled with the emitter via a junction. The LC column stores a different type of particle than the ESI emitter to facilitate better chromatographic and ESI performance.

30 Claims, 6 Drawing Sheets

(56) References Cited

U.S. PATENT DOCUMENTS

| 9,465,014 | B2 | 10/2016 | Dovichi et al. |
| 2004/0245457 | A1 | 12/2004 | Granger |
| 2006/0214099 | A1 | 9/2006 | Oleschuk |
| 2009/0151808 | A1* | 6/2009 | Van Pelt ................ G01N 30/56 141/31 |
| 2010/0193683 | A1* | 8/2010 | Marto ................ G01N 30/6004 264/43 |
| 2014/0110661 | A1* | 4/2014 | Wang .................... H10N 99/00 438/20 |

OTHER PUBLICATIONS

Issaq et al. "The Coupling of Capillary Electrophoresis and Mass Spectrometry in Proteomics", Chapter 8 of Handbook of Capillary and Micropchip Electroporesis and Associated Microtechniques, edited by James P. Landers, Third Edition, Dec. 18, 2007, pp. 295-303.

Covey et al., "Nanospray Electrospray Ionization Development," Chapter 2 of Applied Electrospray Mass Spectrometry, edited by Pramanik et al., Feb. 28, 2002, 59 pages.

Wang et al. "Signal Enhancement for Peptide Analysis in Liquid Chromatography—Electrospray Ionization Mass Spectrometry with Trifluroacetic Acid Containing Mobile Phase by Postcolumn Electrophoretic Mobility Control," Analytical Chemistry, No. 83, 2011, pp. 6163-6168.

Christine L Gatlin et al: "Protein Identification at the Low Femtomole Level from Silver-Stained Gels Using a New Fritless Electrospray Interface for Liquid Chromatography-Microspray and Nanospray Mass Spectrometry", Analytical Biochemistry, Academic Press, Amsterdam, NL, vol. 263, No. 1, Oct. 1, 1998 (Oct. 1, 1998 ), pp. 93-101.

EP Extended Search Report dated Apr. 8, 2022, issued to EP Patent Application No. 21208073.3.

* cited by examiner

PACKED TIP ELECTROSPRAY EMITTER

TECHNICAL FIELD

This disclosure relates to mass spectrometry, and more particularly to a packed tip electrospray ionization (ESI) emitter for a mass spectrometer.

BACKGROUND

A current focus of biological mass spectrometry is the identification, quantification, and structural elucidation of peptides, proteins, and related molecules. In the context of bottom-up proteomics experiments, proteins are subject to proteolytic digestion to break down into fragments of peptides which are then separated, usually with liquid chromatography (LC), before being introduced into an ion source of a mass spectrometer. Typically, the ion source for proteomics experiments implements electrospray ionization (ESI) to ionize the peptide to form ions that can be transported among components of a mass spectrometer.

The physical characteristics of a LC column and an ESI emitter affect analytical performance. For example, stationary phase chemistry, stationary phase particle size, diameter, length, and post-column dead volume of the LC column influence separation efficiency of chromatography. For ESI performance using non-conductive emitters, solution resistances cause a voltage drop that reduces the magnitude of the voltage applied to the tip of the emitter, affecting the formation of ions.

One technique to improve the analytical performance of the LC column and the ESI emitter is to combine the functionality of the emitter with the LC column into a single component, also referred to as a "packed-tip" design or an emitter-enabled capillary column. That is, the LC column can include an end that is pulled to a tip to implement the emitter, resulting in a single structure forming the LC column and the emitter. Due to the integration of the emitter with the LC column in a single structure, the post-column dead volume (i.e., the volume after the LC column and before a detector) is reduced, thereby reducing post-column peak broadening. This results in an increase, or ideal state, in the chromatographic performance.

However, because the aforementioned packed-tip design includes an integration of the LC column with the emitter in a single structure, performance can be degraded if the LC column portion or the emitter portion is not manufactured within the proper specifications. The manufacturing yield can also be reduced from the increased manufacturing complexity of forming both the LC column and the emitter in a single structure.

Additionally, in the packed-tip design, a voltage is applied upstream of the LC column and carried to the emitter tip through the solution path to the tip, or the outlet, of the emitter. This causes the resistance to increase, thus causing a voltage drop that reduces the magnitude of the voltage at the emitter tip. As a result, the strength of the electric field between the emitter tip and inlet of the mass spectrometer is reduced, affecting the formation of ions, and reducing the analytical performance of the ESI emitter. Moreover, ions of the opposite charge from the analytical ions that are formed migrate upstream through the LC column. This results in undesirable electrochemical processes that degrade chromatographic performance.

SUMMARY

One innovative aspect of the subject matter described in this disclosure includes an apparatus for analyzing a sample with a mass spectrometer, comprising: an electrospray ionization (ESI) emitter having first particles disposed within; a junction coupled with the emitter; and a liquid chromatography (LC) column coupled with the junction, the LC column having second particles disposed within, the first particles and the second particles being different types of particles.

In some implementations, the first particles and the second particles are different types of particles.

In some implementations, the first particles and the second particles are a same type of particle.

In some implementations, the first particles disposed within the ESI emitter are not in physical contact with the second particles disposed within the LC column.

In some implementations, the first particles are larger in size than the second particles.

In some implementations, the first particles are silica particles.

In some implementations, the silica particles are porous bare fused silica particles.

In some implementations, the second particles are C18 particles.

In some implementations, the junction is a liquid metal junction.

In some implementations, the apparatus includes an electrical source electrically coupled with the junction and configured to apply a voltage to the junction to operate as an electrode of the ESI emitter.

In some implementations, the first particles are more electrically conductive than the second particles.

In some implementations, the first particles are core-shell particles.

Another innovative aspect of the subject matter described in this disclosure includes a method of operating a mass spectrometer to analyze a sample, comprising: introducing the sample to a liquid chromatography (LC) column having first particles disposed within; eluting the sample from the LC column to an electrospray ionization (ESI) emitter through a junction coupling the LC column with the ESI emitter, the ESI emitter having second particles disposed within; and generating, using the ESI emitter, ions from the sample.

In some implementations, the second particles are larger in size than the first particles.

In some implementations, the second particles are silica particles.

In some implementations, the silica particles are porous bare fused silica particles.

In some implementations, the first particles are C18 particles.

In some implementations, the junction is a liquid metal junction.

In some implementations, the method includes applying an electrical signal from an electrical source to the junction to operate as an anode of the ESI emitter.

In some implementations, the first particles and the second particles are different types of particles.

In some implementations, the first particles and the second particles are a same type of particle.

In some implementations, the first particles disposed within the ESI emitter are not in physical contact with the second particles disposed within the LC column.

In some implementations, the second particles are core-shell particles.

In some implementations, the second particles are more electrically conductive than the first particles.

Another innovative aspect of the subject matter described in this disclosure includes an apparatus, comprising: a chromatography column having first particles disposed within; and an electrospray ionization (ESI) emitter having second particles disposed within, and configured to receive the sample from the chromatography column and generate ions from the sample for mass analysis.

In some implementations, the second particles are larger in size than the first particles.

In some implementations, the first particles are C18 particles, and the second particles are porous bare fused silica particles.

In some implementations, the apparatus includes a junction disposed between the chromatography column and the ESI emitter, the junction configured to serve as an electrode for the ESI emitter.

In some implementations, the first particles and the second particles are different types of particles.

In some implementations, the first particles and the second particles are a same type of particle.

In some implementations, the second particles disposed within the ESI emitter are not in physical contact with the first particles disposed within the LC column.

In some implementations, the second particles are core-shell particles, and the first particles are C18 particles.

Another innovative aspect of the subject matter described in this disclosure includes an apparatus, comprising: an electrospray ionization (ESI) emitter; and particles disposed within the emitter.

In some implementations, the particles are one or both of: core-shell particles or porous bare fused silica particles.

In some implementations, the apparatus includes a liquid-metal junction adjacent to the ESI emitter and serve as an electrode of the ESI emitter.

DETAILED DESCRIPTION

Some of the material described in this disclosure includes electrospray ionization (ESI) emitters for mass spectrometers. In one example, a mixture including peptides is introduced into a liquid chromatography (LC) system such that different peptides in the mixture are separated and introduced into a mass spectrometer for analysis at different times. As a peptide is introduced into the mass spectrometer, the peptide and other co-eluting substances are ionized using electrospray ionization (ESI) to produce ions that are transported among the components of the mass spectrometer for mass analysis.

As described later in this disclosure, a packed-tip emitter for ESI can include a LC column coupled with an emitter via a post-column liquid metal junction. That is, the packed-tip emitter can include an integration of the emitter structure with the LC column structure by coupling both on opposing ends of the post-column liquid metal junction to form a component from separate LC column and emitter structures. Thus, discrete structures for the LC column and emitter can be fabricated separately, and attached to form a single component providing both the LC column and the emitter on opposite ends of the post-column liquid metal junction. Upon degradation of the emitter, it can also be separately replaced. This provides an easier manufacturing solution and, therefore, improves the manufacturing yield as well as reducing the cost of performing an experiment.

Due to the separate structures, the LC column and the emitter can be packed with different particles. For example, the LC column might be packed with C18 particles to facilitate improved LC performance, whereas the emitter can be packed with porous bare fused silica particles to facilitate LC performance and emitter performance. After packing the separate structures, the packed-tip emitter and LC column structures can be assembled with the liquid metal junction. Thus, the chromatographic performance can be improved by providing appropriate particles in the respective structures. This is different than other devices with separate LC columns and emitters that typically do not include particles within the emitter.

Additionally, a voltage may be applied to the post-column liquid metal junction rather than upstream (e.g., at the inlet of the LC column) as in other packed-tip emitters. This can provide a significantly lower solution resistance from the post-column liquid metal junction (as an anode of the ESI source with positive mode electrospray ionization) to the inlet of the mass spectrometer (as a cathode). By contrast, in other packed-tip emitters, the solution resistance is higher because, without the post-column liquid metal junction, the voltage is applied at the inlet of the entire structure (i.e., upstream at the inlet of the LC column). As previously discussed regarding other packed-tip emitters, this causes the voltage at the emitter tip to be lower (possibly altering the spray mode) and causes the migration of counterions within the LC column, resulting in the performance of ESI and LC, respectively, to decrease. Therefore, performance degradations can be reduced with the post-column liquid metal junction.

Furthermore, by utilizing separate structures for the LC column and emitter, the length of the LC column can be varied (e.g., increased) without impacting the solution resistance. The internal diameter of the emitter can also be increased, while decreasing the length of the emitter, to reduce resistance and improve ESI performance.

Figure 1:
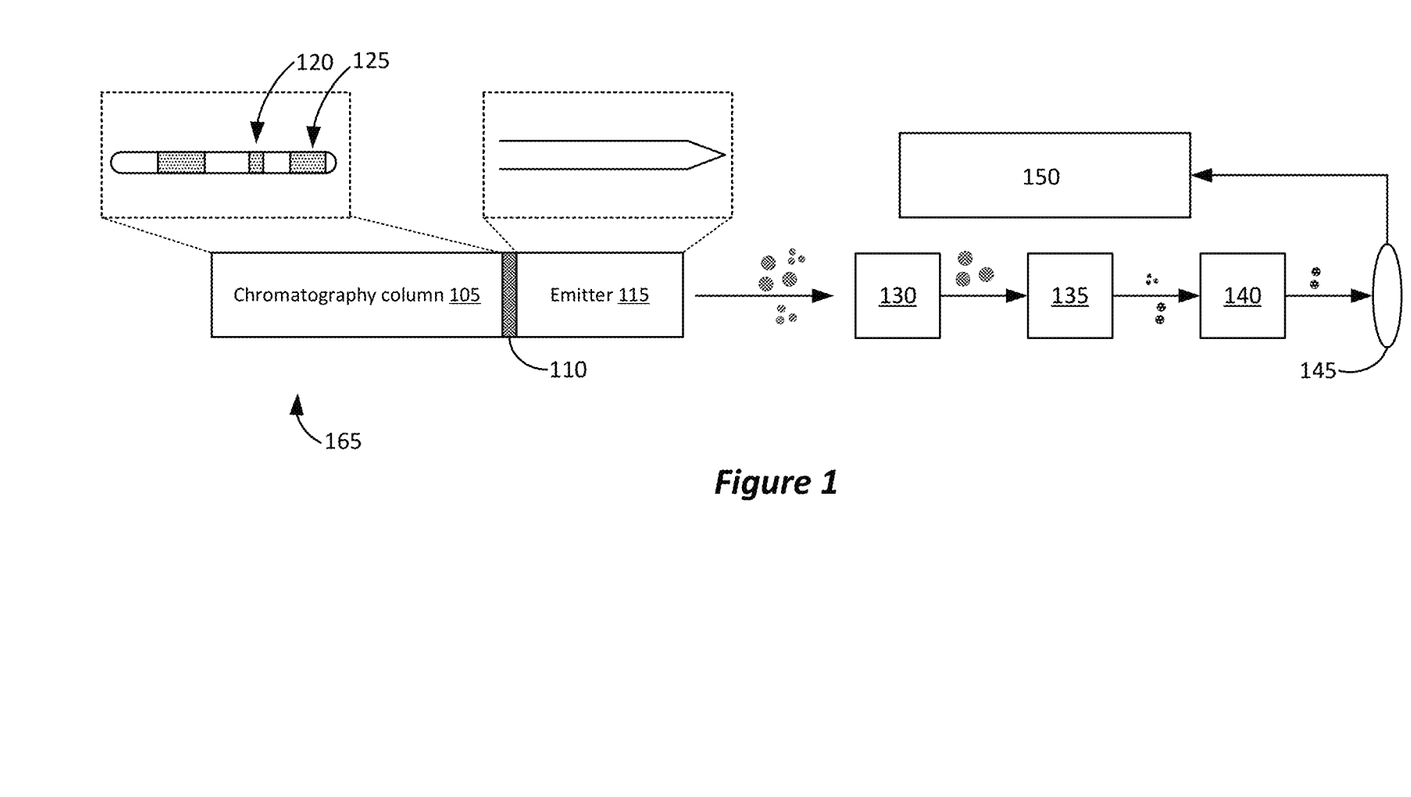
FIG. 1 illustrates an example of a packed-tip emitter for use with a mass spectrometer.

In more detail, FIG. 1 illustrates an example of a packed-tip emitter for use with a mass spectrometer. In FIG. 1, packed-tip emitter 165 includes chromatography column 105, post-column liquid metal junction 110, and emitter 115.

In a bottom-up proteomics experiment, a protein is subject to digestion to form fragments of the protein, or peptides. The sample is then provided to an inlet of chromatography column 105 to separate the various components (e.g., peptides) of the sample via high performance liquid chromatography (HPLC). This results in different groups of peptides being introduced at the outlet of chromatography column 105 at different times, as depicted with peptides 120 and 125 in FIG. 1 depicted at different positions (or separated in space) along a flow path within chromatography column 105.

Next, a group of peptides (e.g., peptides 125) can elute from chromatography column 105 to emitter 115. Emitter 115 is a packed-tip emitter disposed on the opposite side of post-column liquid metal junction 110 from chromatography column 105. Emitter 105 is an emitter of an electrospray ionization (ESI) source type that is used to ionize the peptides to form precursor ions. The ESI source can ionize a sample under analysis by removing or adding charge-carrying entities (e.g., hydrogen nuclei or electrons) to or from the sample to provide the sample with a positive or negative charge.

The precursor ions are then transported via ion optics to mass selector 130. Mass selector 130 may take the form, in one example, of a quadrupole mass filter in which the amplitudes of the radio-frequency (RF) and resolving direct current (DC) voltages are adjusted such that only ions within a narrow range of m/z values are transmitted. Alternatively, mass selector 130 may be any suitable device capable of isolating ions within a mass-to-charge ratio (m/z) window of interest, such as an analytical ion trap or time-of-flight (TOF) mass analyzer. As depicted in FIG. 1, some of the precursor ions of the peptide are thus mass selected and passed onwards to fragmentation cell 135. In other words, some of the precursor ion species are mass isolated.

Fragmentation cell 135 receives the precursor ions from mass analyzer 130 and fragments, or breaks up, the precursor ions into smaller product ions. Fragmentation is often performed on larger molecules, such as peptides, to allow for more detailed understanding of the structural composition of the peptide. Fragmentation cell 135 can be implemented using many different types of disassociation techniques including collision-induced disassociation (CID), surface-induced dissociation (SID), electron-capture dissociation (ECD), electron-transfer dissociation (ETD), negative electron-transfer dissociation (NETD), electron-detachment dissociation (EDD), photodissociation, higher-energy C-trap dissociation (HCD), etc.

Next, the resulting product ions are subjected to mass analysis to yield an experimental mass spectrum. For example, in FIG. 1, the product ions formed by fragmentation cell 135 are provided to a mass analyzer 140, mass separated, and then provided to detector 145. Mass analyzer 140 can be any suitable device for separating ions according to their mass-to-charge ratios, including (without limitation) an orbital electrostatic trap, analytical quadrupole ion trap, Fourier Transform-Ion Cyclotron Resonance (FT-ICR) analyzer, TOF mass analyzer, or a quadrupole mass filter.

Detector 145 detects induced charge or current produced when the product ions provided by mass analyzer 140 pass by or hit a surface of detector 145. Thus, detector 145 generates signals representative of the m/z of the product ions. These signals can be provided to controller 150, which can then generate a mass spectrum using the detected signals.

In the example of FIG. 1, the mass spectrometer is a tandem mass spectrometer configured to implement a single stage of mass isolation and fragmentation, as indicated with the arrangement of fragmentation cell 135 between mass selector 130 and mass analyzer 140. This is often referred to as MS/MS or MS2 mass spectrometry. In certain implementations, it may be desirable to perform further stages of isolation and fragmentation of generations of product ions (e.g., MS3, MS4, MS5, etc. wherein n is a positive integer). In such cases, the components of the mass spectrometer may be configured to cause the additional isolation/fragmentation operations. For example, mass analyzer 140 may be an analytical quadrupole ion trap mass analyzer that, in addition to performing the mass separation function for acquiring mass spectra, is also capable of executing steps of mass isolation and fragmentation. However, other types of mass spectrometers other than tandem mass spectrometers can also be used with packed-tip emitter 165.

Figure 2:
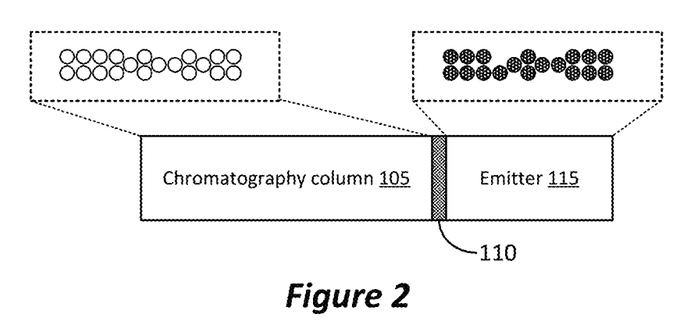
FIG. 2 illustrates an example of particles disposed within a chromatography column and emitter of a packed-tip emitter.

To improve chromatographic and ESI performance, chromatography column 105 and emitter 115 can be packed with different particles. FIG. 2 illustrates an example of particles disposed within a chromatography column and emitter of a packed-tip emitter. In FIG. 2, chromatography column 105 is packed with C18 particles (or the majority of particles within chromatography column 105 are C18 particles). In some implementations, the column might have two or more sections packed with different particles to implement a 2-D chromatographic separation. C18 particles are molecules that include at least 18 carbon atoms and serve as the stationary phase of chromatography column 105 to separate the components of the mixture. However, emitter 115 can be packed with a different type of particle (or the majority of particles in emitter 115 are the different type of particle) than chromatography column 105. For example, rather than being packed with C18 particles, emitter 115 in FIG. 2 is packed with silica particles, and more particularly, can be packed with porous bare fused silica particles.

The different particles can be selected to improve chromatographic performance of chromatography column 105 and the ESI performance of emitter 115. For example, as previously discussed, stationary phase chemistry, stationary phase particle size, diameter of chromatography column 105, length of chromatography column 105, and post-column dead volume of chromatography column 105 influence separation efficiency of chromatography. The particles within emitter 115 can also be selected such that post-column dead space is reduced because the volume within the internal volume of emitter 115 is partially filled, resulting in a reduction in post-column peak broadening to improve the chromatographic performance. The particles within emitter 115, such as porous bare fused silica particles, can be chromatographically inert or provide no or little chemical interactions with the samples. The particles can be packed into the respective structures via high pressure.

The different types of particles disposed within the separate structures also results in the particles having different attributes. For example, particles disposed within emitter 115 can be larger in size (e.g., larger in diameter, larger in volume, have a larger largest dimension, etc.) than the particles disposed within chromatography column 105. In one example, the particles within emitter 115 can be spherical (or relatively spherical) particles with a diameter of 10 microns and the particles within chromatography column 105 can be spherical (or relatively spherical) particles with a diameter of 2 microns.

The particles within emitter 115 can provide reduced diffusion or a reduced path length when compared to the particles within chromatography column 105. That is, the particles within emitter 115 can reduce or minimize the path turns as the peptides are transported through the emitter such that the peptides move through emitter 115 faster than chromatography column 105. For example, non-retentive or less retentive particles can be disposed within emitter 115 compared to the particles within chromatography column 105 such that the retention time of the peptides within chromatography column 105 is longer than within emitter 115.

Another comparison between the particles can be made in relation to porosity. The particles within emitter 115 can also be more porous than the particles within chromatography column 105 to improve the conductivity between the anode and the emitter tip. The examples described herein are in positive mode electrospray ionization in which the anode is post-column liquid metal junction 110 and the inlet of the mass spectrometer is the cathode. However, in negative mode electrospray, post-column liquid metal junction 110 would be the cathode and the inlet of the mass spectrometer would be the anode. That is, the type of electrical terminal or electrode that post-column liquid metal junction 110 and the inlet of the mass spectrometer are is based on the charge mode of electrospray ionization.

The particles can also have different electrical conductivity. For example, the particles within emitter 115 can be more electrically conductive than the particles within chromatography column 105. Using particles with higher electrical conductivity within emitter 115 decreases the electrical resistance from post-column liquid metal junction 110 (which serves as an anode in positive mode electrospray ionization) through emitter 115 and to the tip of the emitter 115, as discussed more later.

The particles within emitter 115 can be a composite, for example, core-shell particles having a solid core and a porous shell around the core (i.e., the porous shell being more porous than the solid core). A core-shell particle would have a reduced path length compared to fully porous particles that may occupy the LC column. The composition of the particle that is the core or the shell can be adjusted to achieve the desired performance. For example, two particles can have the same diameter (if spherical), but different sized cores. The particle with the larger core would have a reduced multiple path term compared to the particle with the smaller core because the shell of the particle with the larger core would be smaller than the particle with the smaller core.

Thus, using different particles (or majorities of particles) within emitter 115 and chromatography column 105 improves performance, with packing particles in emitter 115 reducing post-column dead volume. Manufacturing yield also improves due to the ability to fabricate separate structures. Additionally, placing post-column liquid metal junction 110 downstream from chromatography column 105, and upstream from emitter 115, provides further performance improvements, as explained below.

In general, an emitter and chromatography column can provide better performance by: (i) having a charge separation process at the emitter tip independent from the electrochemistry that occurs at the anode (ii) reducing solution resistance between the anode and the emitter tip, (iii) reducing the post-column dead volume, (iv) adjusting the length of the chromatography column without impacting the solution resistance, and (v) applying a sheath gas to further reduce the solution resistance. Using the techniques described herein, these can be achieved.

The post-column dead volume is reduced by packing particles within emitter 115 of the packed-tip emitter, as discussed above. Additionally, post-column liquid metal junction 110 is positioned between chromatography column 105 and emitter 115 and serves as an anode for the ESI source. Thus, a voltage is applied to post-column liquid metal junction 110 (i.e., downstream from chromatography column 105). This results in a reduced solution resistance within the packed-tip emitter, improving ESI and chromatography performance.

Post-column liquid metal junction 110 can be composed of titanium, platinum, gold, or other electrically conductive material. In some implementations, post-column liquid metal junction 110 can be largely made of plastic or other non-conductive material, but include a conductive electrical terminal. Thus, a conductive material can be in physical and electrical contact with the sample as it elutes from the LC column. Additionally, post-column liquid metal junction 110 can physically separate the particles within chromatography column 105 and emitter 15 such that the particles within chromatography column 105 do not touch or physically contact the particles within emitter 115.

Figure 5A:
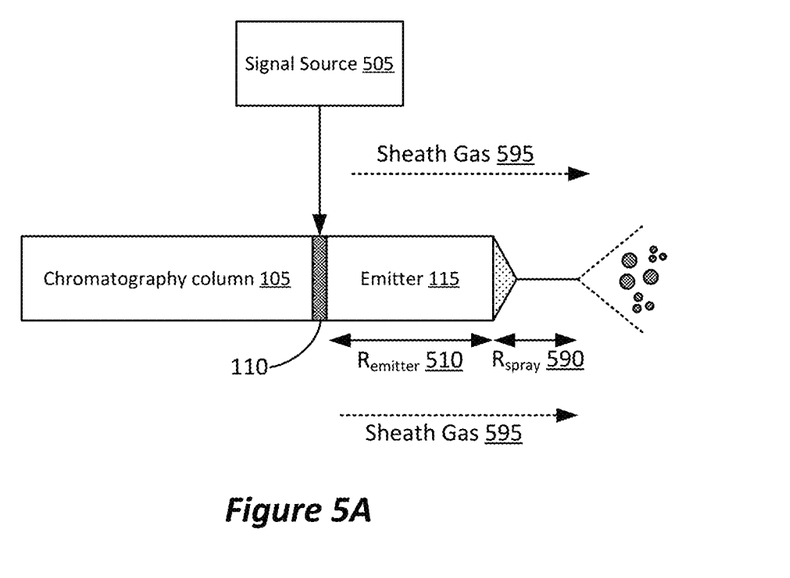
FIGS. 5A and 5B illustrate examples of resistances within a packed-tip emitter.
Figure 5B:
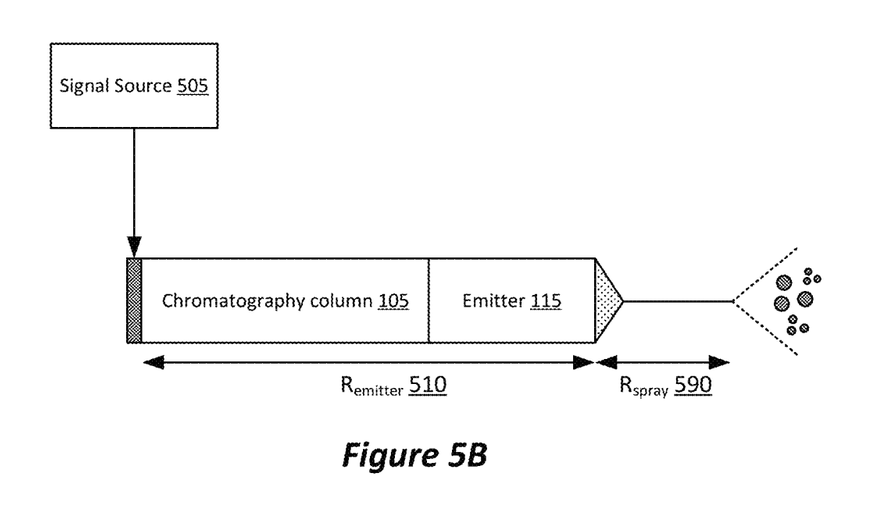

In more detail, FIGS. 5A and 5B illustrate examples of resistances within a packed-tip emitter. In FIG. 5A, signal source 505 applies a voltage to post-column liquid metal junction 110 at a position between chromatography column 105 and emitter 115. As the solution including the sample elutes from chromatography column 105 into emitter 115, the amount of the solution that contributes to $R_{emitter}$ 510 (i.e., the solution resistance modeled as the path through emitter 115) is not affected by the length of chromatography column 105. Thus, the length of chromatography column 105 can be increased to improve chromatographic performance without affecting ESI performance.

By contrast, in FIG. 5B, signal source 505 applies the voltage to an anode upstream from chromatography column 105, as in other types of packed-tip emitters. As depicted, $R_{emitter}$ 510 includes the path through chromatographic column 105, which significantly increases resistance. Thus, ESI performance is decreased.

Specifically, resistance of a solution within the packed-tip emitter is defined by the equation $R=(\rho*L)/A$, wherein R is resistance, $\rho$ is resistivity, L is length, and A is an inner cross-sectional area. At low flow rates, resistance is often in the 1-10 giga-ohm (GΩ) range. When performing separation at a nano-flow rate (e.g., having a spray current of around 100 nanoamps (nA)), a voltage drop occurs from the anode to the tip of the emitter based on the resistance. Thus, a lower voltage than what is applied to the post-column liquid metal junction occurs at the tip of the emitter if $R_{emitter}$ 510 is higher as in FIG. 5B.

A lower voltage at the tip of the emitter affects the spray mode of the ESI source. As voltage is increased, different operational modes (i.e., how the liquid physically forms at the output of the emitter) are transitioned through, for example, a pulsating regime in which erratic droplet ejection occurs at high frequencies, and ultimately to a stable jet regime in which charged droplets are generated from an electrified liquid cone, also known as a Taylor cone, that emanates from the emitter outer diameter. The stable jet regime provides a more stable, reproducible and sensitive electrospray mode for analytical experiments. When in the stable jet regime, a thin flow of the solution forms from the apex of the Taylor cone and towards the inlet of the mass spectrometer. A charged aerosol is generated from the thin flow which undergoes fission and desolvation to ultimately yield gas phase ions for the mass spectrometer. However, if $R_{emitter}$ 510 is higher (as in FIG. 5B), then the voltage at the tip of the emitter might be lower than expected, resulting in being out of the stable jet regime, or in a lower performance region of the stable jet regime. To compensate, the voltage applied at the anode may be increased. But, if $R_{emitter}$ 510 is lower (as in FIG. 5A), then a lower voltage is needed to reach the stable jet regime.

In FIG. 5A, $R_{emitter}$ 510 is lower than in FIG. 5B due to using the post-column liquid junction, which causes the length in the above equation to lower. Moreover, the cross-sectional area of the inner diameter of emitter 115 can be increased to further lower the resistance. For example, the largest internal diameter can be greater than 20 microns (with the tip of the emitter being pulled to less than or equal to 15 microns). The length of the chromatography column can also be increased without impacting resistance.

In one example, the LC column length can be 5 centimeters (cm) to 5 meters (m) and the internal diameter of the LC column can be from 20 μm to 1 millimeter (mm). In some scenarios, a LC column length from 5 cm to 100 cm and the LC column internal diameter from 50 micrometers (μm) to 500 μm provides substantial performance improvements. Moreover, the internal diameter of the inlet of the emitter might range from 10 μm to 75 μm, and the tip of the emitter might range from 5 μm to 20 μm.

Moreover, the implementation of FIG. 5A also provides isolation of the charge separation process performed by emitter 115 from the electrochemistry that may occur inside the chromatography column 105. In particular, electrochemical charge formation occurs at post-column liquid metal junction 110 when a high voltage is applied. Charge migration towards the apex of the Taylor cone occurs, forming an aerosol that transports droplets including the molecules of the sample (e.g., peptides), and desolvation of the charged droplets occurs towards the cathode, yielding gas phase ions for intake into the mass spectrometer as the precursor ions in the example of tandem MS, as previously discussed. If positive ions are provided to the inlet of the mass spectrometer, then negative ions (i.e., the opposite polarity) migrate upstream opposite of the analytical sample flow to maintain charge balance and become oxidized at the anode. The rate of oxidation limits the amount of positive ion current that can be generated and, therefore, this limits the performance of ESI. Further, because the negative ions migrate towards the anode, the negative ions can cause unwanted electrochromatography performed within chromatographic column 105 if the anode is upstream of chromatographic column 105 as in FIG. 5B rather than downstream as in FIG. 5A.

Often, a sheath gas (e.g., nitrogen) is applied to the solution at the outlet of emitter 115. By constraining the volume of the spray, $R_{spray}$ 590 (i.e., the resistance caused by the filament), the resistance is also reduced, further improving ESI performance. For example, application or flow of sheath gas 595 around emitter 115 in FIG. 5A can also reduce $R_{spray}$ 590. Compared to FIG. 5B without the use of sheath gas 595, the liquid filament formed at the tip, or outlet, of emitter 115 in FIG. 5A is shorter in length.

Figure 7:
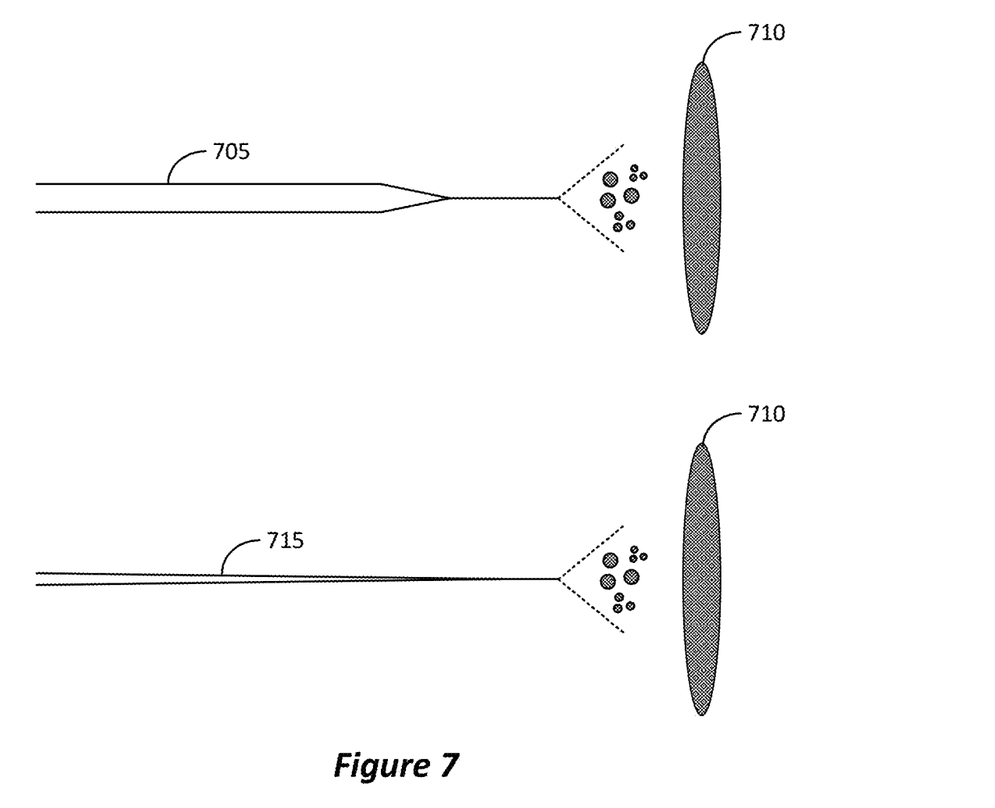
FIG. 7 illustrates examples of a tapered emitter and a pulled tip emitter.

The configuration of emitters 115 in FIGS. 5A and 5B can be different. FIG. 7 illustrates examples of a tapered emitter and a pulled tip emitter. In FIG. 7, pulled tip emitter 705 can be the type of emitter used in the example of FIG. 5B. The external cross-sectional area of pulled tip emitter 705 can be relatively the same along the length of packed tip emitter 705, and then quickly taper to a smaller tip in vicinity of mass spectrometer inlet 710. By contrast, tapered emitter 715 can be implemented in the example of FIG. 5A and includes a varying external cross-sectional area (or a varying external diameter) along most or all of the length of emitter 715 while maintaining a constant or relatively constant internal diameter. This would increase the resistance, but $R_{emitter}$ 510 would still be less due to post-column liquid junction 110, as previously discussed. In one example, the internal diameter of tapered emitter 715 ranges from 10 to 15 micrometers (μm). The internal diameter of pulled tip emitter 705 might be mostly (e.g., over 50% of the length of pulled tip emitter 705) 50 μm to 75 μm before tapering down at the tip to 10 μm.

In some implementations, emitter 115 in FIGS. 1 and 2 can be packed with different particles. For example, close to the tip or outlet, one type of particle may be packed. Another particle might be packed in the remaining volume of emitter 115. Thus, larger or more porous particles might be disposed closer to the tip, and smaller or less porous particles might be packed closer to the post-column liquid metal junction.

Experimentation shows that the solution resistance (e.g., $R_{emitter}$ 510 in FIG. 5A) and the spindle resistance (e.g., $R_{spray}$ 590 in FIG. 5A) are lower for the implementation of FIG. 5A in comparison to the implementation of FIG. 5B. For example, an emitter with a 75 μm internal diameter and 40 mm length, and packed with bare fused silica particles of approximately 10 μm in diameter, has half the resistance of an open tubular emitter that has a diameter of 20 μm and length of 35 mm. The spindle resistance is also lowered by over 1 giga-Ohm. The decrease in resistances significantly can improve the performance, as previously discussed.

Figure 3:
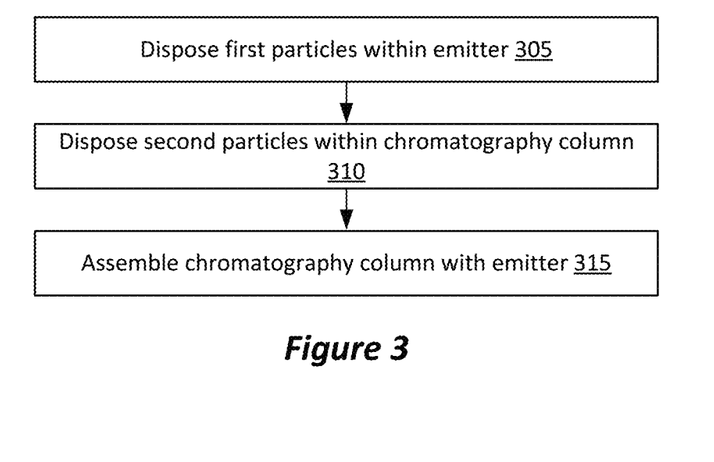
FIG. 3 illustrates an example of a block diagram for assembling a packed-tip emitter.

FIG. 3 illustrates an example of a block diagram for assembling a packed-tip emitter. In FIG. 3, particles can be disposed within the emitter (305). For example, the emitter can be cut to a particular length and coupled with a packing reservoir via a high-pressure connection. Silica particles (or porous bare fused silica particles, core-shell particles, or any other types of particles described herein) can be packed via high pressure into emitter 115 in FIGS. 1 and 2. In one example, a slurry of silica particles and organic solvent can be pipetted into the packing reservoir and pushed within the emitter using high pressure liquid chromatography (HPLC). Next particles can be disposed within the chromatography column (310). For example, C18 particles can be packed via high pressure into chromatography column 105 in FIGS. 1 and 2. Next, the chromatography column can be assembled with the emitter (315). For example, the chromatography column can be positioned on one side of the liquid metal junction, and the emitter can be positioned on the opposing side of the liquid metal junction.

Figure 4:
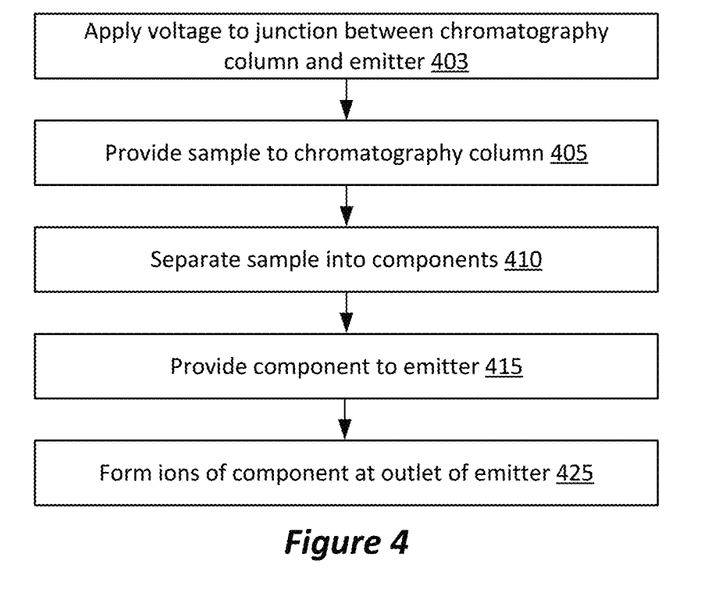
FIG. 4 illustrates an example of operating a packed-tip emitter.

FIG. 4 illustrates an example of operating a packed-tip emitter. In FIG. 4, a voltage is applied to a junction between a chromatography column and an emitter of an ESI source (403). For example, in FIG. 1, a voltage is applied to a post-column liquid metal junction 110. Next, a sample is provided to the chromatography column (405). For example, in FIG. 1, a sample is provided to an inlet of chromatography column 105. This causes the sample to be separated into different components (410) and different components elute out of the outlet of the chromatography column at different times for providing to an emitter (415). For example, in FIG. 1, peptides elute from chromatography column 105, through post-column liquid metal junction 110, and into emitter 115. Ions of the component are then formed at the outlet of the emitter (425). For example, in FIG. 1, the peptides are brought to the tip of emitter 115 and dispersed into an aerosol via a Taylor cone. An inlet of the mass spectrometer samples the aerosol through a capillary that serves as a cathode and at a voltage to generate an electrical field in conjunction with the voltage applied at the anode (i.e., liquid metal junction 110). Over time, the aerosol droplets desolvate and form precursor ions for mass analysis.

The examples describe techniques for analyzing peptides, however, other biomolecules can be used. For example, in addition to proteins and their peptides, other types of biomolecules that can be used with the techniques include lipids, nucleic acids, metabolites, oligosaccharides, polysaccharides, and the like. Moreover, other large molecules other than biomolecules can be identified, in addition to small molecules. Thus, the experimental mass spectrum can be generated for many different types of molecules.

Figure 6:
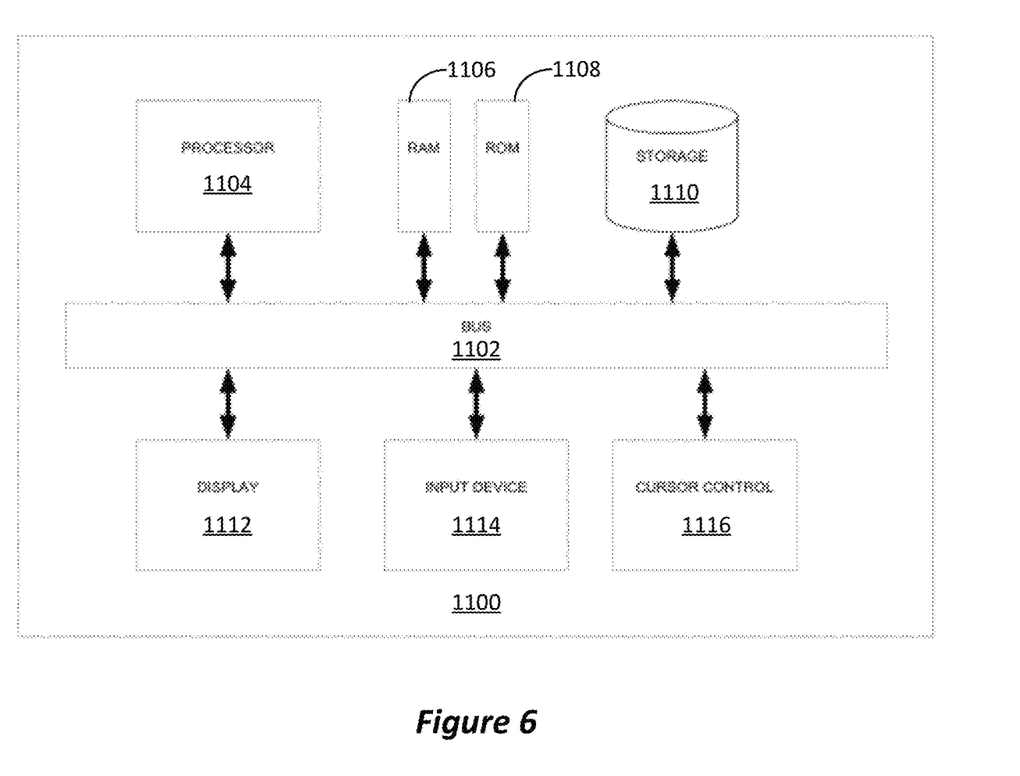
FIG. 6 illustrates an example of an electronic device which may be used to implement some of the examples.

FIG. 6 illustrates an example of an electronic device which may be used to implement some of the examples. For example, the electronic device in FIG. 6 can be controller 150 in FIG. 1. The electronic device of FIG. 6 can store or use a computer program product including one or more non-transitory computer-readable media having computer programs instructed stored therein, the computer program instructions being configured such that, when executed by one or more computing devices, the computer program instructions cause the one or more computing devices to perform the techniques described herein.

In FIG. 6, computer system 1100 can implement any of the methods or techniques described herein. For example, as previously discussed, computer system 1100 can implement controller 150 in FIG. 1. Thus, the operation of components of the associated mass spectrometer may be adjusted in accordance with calculations or determinations made by computer system 1100. In various embodiments, computer system 1100 can include a bus 1102 or other communication mechanism for communicating information, and a processor 1104 coupled with bus 1102 for processing information. In various embodiments, computer system 1100 can also include a memory 1106, which can be a random-access memory (RAM) or other dynamic storage device, coupled to bus 1102, and instructions to be executed by processor 1104. Memory 1106 also can be used for storing temporary variables or other intermediate information during execution of instructions to be executed by processor 1104. In various embodiments, computer system 1100 can further include a read only memory (ROM) 1108 or other static storage device coupled to bus 1102 for storing static information and instructions for processor 1104. A storage device 1110, such as a magnetic disk or optical disk, can be provided and coupled to bus 1102 for storing information and instructions.

In various embodiments, computer system 1100 can be coupled via bus 1102 to a display 1112, such as a cathode ray tube (CRT) or liquid crystal display (LCD), for displaying information to a computer user. An input device 1114, including alphanumeric and other keys, can be coupled to bus 1102 for communicating information and command selections to processor 1104. Another type of user input device is a cursor control 1116, such as a mouse, a trackball or cursor direction keys for communicating direction information and command selections to processor 1104 and for controlling cursor movement on display 1112. This input device typically has two degrees of freedom in two axes, a first axis (i.e., x) and a second axis (i.e., y), that allows the device to specify positions in a plane.

A computer system 1100 can perform the techniques described herein. Consistent with certain implementations, results can be provided by computer system 1100 in response to processor 1104 executing one or more sequences of one or more instructions contained in memory 1106. Such instructions can be read into memory 1106 from another computer-readable medium, such as storage device 1110. Execution of the sequences of instructions contained in memory 1106 can cause processor 1104 to perform the processes described herein. In various embodiments, instructions in the memory can sequence the use of various combinations of logic gates available within the processor to perform the processes describe herein. Alternatively, hard-wired circuitry can be used in place of or in combination with software instructions to implement the present teachings. In various embodiments, the hard-wired circuitry can include the necessary logic gates, operated in the necessary sequence to perform the processes described herein. Thus, implementations described herein are not limited to any specific combination of hardware circuitry and software.

The term "computer-readable medium" as used herein refers to any media that participates in providing instructions to processor 1104 for execution. Such a medium can take many forms, including but not limited to, non-volatile media, volatile media, and transmission media. Examples of non-volatile media can include, but are not limited to, optical or magnetic disks, such as storage device 1110. Examples of volatile media can include, but are not limited to, dynamic memory, such as memory 1106. Examples of transmission media can include, but are not limited to, coaxial cables, copper wire, and fiber optics, including the wires that comprise bus 1102.

Common forms of non-transitory computer-readable media include, for example, a floppy disk, a flexible disk, hard disk, magnetic tape, or any other magnetic medium, a CD-ROM, any other optical medium, punch cards, paper tape, any other physical medium with patterns of holes, a RAM, PROM, and EPROM, a FLASH-EPROM, any other memory chip or cartridge, or any other tangible medium from which a computer can read.

In accordance with various embodiments, instructions configured to be executed by a processor to perform a method are stored on a computer-readable medium. The computer-readable medium can be a device that stores digital information. For example, a computer-readable medium includes a compact disc read-only memory (CD-ROM) as is known in the art for storing software. The computer-readable medium is accessed by a processor suitable for executing instructions configured to be executed.

In various embodiments, the methods of the present teachings may be implemented in a software program and applications written in conventional programming languages such as C, C++, etc.

While the techniques are described in conjunction with various implementations or embodiments, it is not intended that the techniques be limited to such embodiments. On the contrary, the techniques encompass various alternatives, modifications, and equivalents, as will be appreciated by those of skill in the art.

Further, in describing various embodiments, the specification may have presented a method and/or process as a particular sequence of steps. However, to the extent that the method or process does not rely on the particular order of steps set forth herein, the method or process should not be limited to the particular sequence of steps described. As one of ordinary skill in the art would appreciate, other sequences of steps may be possible. Therefore, the particular order of the steps set forth in the specification should not be construed as limitations on the claims. In addition, the claims directed to the method and/or process should not be limited to the performance of their steps in the order written, and one skilled in the art can readily appreciate that the sequences may be varied and still remain within the spirit and scope of the various embodiments.

The embodiments described herein, can be practiced with other computer system configurations including hand-held devices, microprocessor systems, microprocessor-based or programmable consumer electronics, minicomputers, mainframe computers and the like. The embodiments can also be practiced in distributing computing environments where tasks are performed by remote processing devices that are linked through a network.

It should also be understood that the embodiments described herein can employ various computer-implemented operations involving data stored in computer systems. These operations are those requiring physical manipulation of physical quantities. Usually, though not necessarily, these quantities take the form of electrical or magnetic signals capable of being stored, transferred, combined, compared, and otherwise manipulated. Further, the manipulations performed are often referred to in terms, such as producing, identifying, determining, or comparing.

Any of the operations that form part of the embodiments described herein are useful machine operations. The embodiments, described herein, also relate to a device or an apparatus for performing these operations. The systems and methods described herein can be specially constructed for the required purposes or it may be a general purpose computer selectively activated or configured by a computer program stored in the computer. In particular, various general purpose machines may be used with computer programs written in accordance with the teachings herein, or it may be more convenient to construct a more specialized apparatus to perform the required operations.

Certain embodiments can also be embodied as computer readable code on a computer readable medium. The computer readable medium is any data storage device that can store data, which can thereafter be read by a computer system. Examples of the computer readable medium include hard drives, network attached storage (NAS), read-only memory, random-access memory, CD-ROMs, CD-Rs, CD-RWs, magnetic tapes, and other optical and non-optical data storage devices. The computer readable medium can also be distributed over a network coupled computer systems so that the computer readable code is stored and executed in a distributed fashion.

We claim:

1. An apparatus for analyzing a sample with a mass spectrometer, comprising:
an electrospray ionization (ESI) emitter having first particles disposed within;
a junction coupled with the emitter; and
a liquid chromatography (LC) column coupled with the junction, the LC column having second particles disposed within, the first particles and the second particles being different types of particles, and wherein the first particles are more electrically conductive than the second particles.

2. The apparatus of claim 1, wherein the first particles and the second particles are different types of particles.

3. The apparatus of claim 1, wherein the first particles and the second particles are a same type of particle.

4. The apparatus of claim 1, wherein the first particles disposed within the ESI emitter are not in physical contact with the second particles disposed within the LC column.

5. The apparatus of claim 1, wherein the first particles are larger in size than the second particles.

6. The apparatus of claim 1, wherein the first particles are silica particles.

7. The apparatus of claim 6, wherein the silica particles are porous bare fused silica particles.

8. The apparatus of claim 6, wherein the second particles are C18 particles.

9. The apparatus of claim 1, wherein the junction is a liquid metal junction.

10. The apparatus of claim 1, further comprising:
an electrical source electrically coupled with the junction and configured to apply a voltage to the junction to operate as an electrode of the ESI emitter.

11. The apparatus of claim 1, wherein the first particles are core-shell particles.

12. A method of operating a mass spectrometer to analyze a sample, comprising:
introducing the sample to a liquid chromatography (LC) column having first particles disposed within;
eluting the sample from the LC column to an electrospray ionization (ESI) emitter through a junction coupling the LC column with the ESI emitter, the ESI emitter having second particles disposed within, wherein the first particles are more electrically conductive than the second particles; and
generating, using the ESI emitter, ions from the sample.

13. The method of claim 12, wherein the second particles are larger in size than the first particles.

14. The method of claim 12, wherein the second particles are silica particles.

15. The method of claim 14, wherein the silica particles are porous bare fused silica particles.

16. The method of claim 14, wherein the first particles are C18 particles.

17. The method of claim 12, wherein the junction is a liquid metal junction.

18. The method of claim 12, further comprising:
applying an electrical signal from an electrical source to the junction to operate as an anode of the ESI emitter.

19. The method of claim 12, wherein the first particles and the second particles are different types of particles.

20. The method of claim 12, wherein the first particles and the second particles are a same type of particle.

21. The method of claim 12, wherein the second particles disposed within the ESI emitter are not in physical contact with the first particles disposed within the LC column.

22. The method of claim 12, wherein the second particles are core-shell particles.

23. An apparatus, comprising:
a chromatography column having first particles disposed within; and
an electrospray ionization (ESI) emitter having second particles disposed within, and configured to receive a sample from the chromatography column and generate ions from the sample for mass analysis, wherein the first particles are more electrically conductive than the second particles.

24. The apparatus of claim 23, wherein the second particles are larger in size than the first particles.

25. The apparatus of claim 23, wherein the first particles are C18 particles, and the second particles are porous bare fused silica particles.

26. The apparatus of claim 23, further comprising:
a junction disposed between the chromatography column and the ESI emitter, the junction configured to serve as an electrode for the ESI emitter.

27. The apparatus of claim 23, wherein the first particles and the second particles are different types of particles.

28. The apparatus of claim 23, wherein the first particles and the second particles are a same type of particle.

29. The apparatus of claim 23, wherein the second particles disposed within the ESI emitter are not in physical contact with the first particles disposed within the LC column.

30. The apparatus of claim 23, wherein the second particles are core-shell particles, and the first particles are C18 particles.

* * * * *